(12) United States Patent
Tsujita et al.

(10) Patent No.: US 7,331,234 B2
(45) Date of Patent: Feb. 19, 2008

(54) ULTRASONIC IMAGING METHOD AND ULTRASONIC IMAGING APPARATUS

(75) Inventors: Kazuhiro Tsujita, Kaisei-machi (JP); Tomoo Satoh, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 824 days.

(21) Appl. No.: 10/701,555

(22) Filed: Nov. 6, 2003

(65) Prior Publication Data
US 2004/0102704 A1 May 27, 2004

(30) Foreign Application Priority Data
Nov. 13, 2002 (JP) .............................. 2002-329822

(51) Int. Cl.
*G01N 29/00* (2006.01)
(52) U.S. Cl. ..................... 73/606; 73/602; 73/628; 600/437; 600/447
(58) Field of Classification Search ............... 73/606, 73/596, 602, 618, 620, 626, 628; 600/437, 600/443, 447; 367/7, 103
See application file for complete search history.

(56) References Cited

U.S. PATENT DOCUMENTS

| | | | | |
|---|---|---|---|---|
| 4,084,582 A * | 4/1978 | Nigam | ......................... | 600/446 |
| 5,123,415 A * | 6/1992 | Daigle | ........................ | 600/447 |
| 5,142,649 A * | 8/1992 | O'Donnell | .................... | 367/7 |
| 6,055,861 A * | 5/2000 | Banta et al. | .................. | 73/626 |
| 6,491,631 B2 * | 12/2002 | Chiao et al. | ................ | 600/443 |
| 6,640,633 B2 * | 11/2003 | Satoh | ........................ | 73/626 |
| 6,716,173 B2 * | 4/2004 | Satoh | ......................... | 600/447 |
| 6,752,762 B1 * | 6/2004 | DeJong et al. | .............. | 600/458 |
| 6,973,831 B2 * | 12/2005 | Satoh | ........................ | 73/618 |
| 2002/0120194 A1 * | 8/2002 | Satoh | ......................... | 600/443 |
| 2006/0036169 A1 * | 2/2006 | Satoh | ......................... | 600/437 |
| 2006/0079780 A1 * | 4/2006 | Karasawa | ................... | 600/447 |

OTHER PUBLICATIONS

Kanda et al.., Digital Ultrasonic Technology, Extra Number of Clinical Radiation, Kanehara & Col., JP, 1998, vol. 43, No. 11.
Dadisen et al., Two-Dimensional Randmom Arrays for Real Time Volumetric Imaging, Ultrasonic Imaging 16, (1994).

* cited by examiner

*Primary Examiner*—Hezron Williams
*Assistant Examiner*—Jacques M. Saint-Surin
(74) *Attorney, Agent, or Firm*—Sughrue Mion, Pllc.

(57) ABSTRACT

An ultrasonic imaging method and apparatus capable of obtaining image information at a high volume rate and improving resolution. The ultrasonic imaging apparatus has an ultrasonic transducer array including plural ultrasonic transducers for transmitting ultrasonic waves in accordance with drive signals and receiving ultrasonic waves to output detection signals; pulsers for supplying the drive signals; an ignition timing controller for controlling the pulsers to respectively transmit plural ultrasonic beams toward plural directions within a predetermined period so that adjacent two ultrasonic beams are separated by 20° or more from each other; receivers for processing the plural detection signals; and plural phase matching units, provided in correspondence with a number of the ultrasonic beams to be transmitted, for performing phase matching on the basis of the processed detection signals so that plural receiving focal points are formed for each of the transmitted plural ultrasonic beams.

14 Claims, 10 Drawing Sheets

ULTRASONIC IMAGING METHOD AND ULTRASONIC IMAGING APPARATUS

BACKGROUND OF THE INVENTION

1. Field of the Invention

The present invention relates to an ultrasonic imaging method and an ultrasonic imaging apparatus for performing diagnosis on internal organs in a living body or nondestructive inspection by using ultrasonic waves.

2. Description of a Related Art

Generally, in an ultrasonic imaging apparatus including an ultrasonic diagnosing apparatus, an industrial defect detecting apparatus, etc., an ultrasonic transducer array including plural ultrasonic transducers having functions of transmitting and receiving ultrasonic waves is used. In the ultrasonic imaging apparatus having the ultrasonic transducer array, image information on an object to be inspected is obtained by scanning the object with a sound beam formed by synthesizing plural ultrasonic waves. Then, a two-dimensional or three-dimensional image on the object is reproduced based on this image information.

In such ultrasonic imaging apparatus, as a method of transmitting and receiving ultrasonic beams by using an ultrasonic transducer array, the following systems (1) and (2) are known. In addition, designing of ultrasonic beams is described in Hiroshi Kanda et al., "DIGITAL ULTRASONIC TECHNOLOGY", Extra Number of Clinical Radiation, KANEHARA & CO., JP, 1998, Vol. 43, No. 11, pp. 1248-1252.

(1) Unidirectional Ultrasonic Beam Transmission—Ultrasonic Echo Divisional Reception System FIG. 14A is a schematic diagram for explanation of an example of a state of transmitting an ultrasonic beam according to a conventional system, and similarly, FIG. 14B is a schematic diagram for explanation of an example of a state of receiving an ultrasonic beam according to a conventional system.

In this system, ultrasonic pulses are intermittently transmitted from respective plural ultrasonic transducers 101 included in an ultrasonic transducer array 100 based on drive signals that are fed from plural pulsers connected to a transmitting unit. As shown in FIG. 14A, this ultrasonic pulse is transmitted from the ultrasonic transducer array 100 toward an object to be inspected, and propagates within the object to form an ultrasonic beam 102. The ultrasonic beam 102 becomes narrower gradually as it travels in a region at a short distance from the position from which the beam is transmitted, narrowest at a focal point F, and gradually broader afterwards. This ultrasonic beam is reflected by a reflector that exists within the object, thereby an ultrasonic echo is generated, and, as shown in FIG. 14B, this ultrasonic echo is received by the ultrasonic transducer array 100. Detection signals outputted from the plural ultrasonic transducers 101 included in the ultrasonic transducer array 100 are accumulated after predetermined delays are given thereto respectively by plural phase matching computing means connected to a receiving unit, and thereby a detection signal with respect to each received ultrasonic beam is obtained. In this example, three received ultrasonic beams 103, 104, and 105 are shown.

(2) Multidirectional Ultrasonic Beam Transmission—Ultrasonic Echo Non-divisional Reception System FIG. 15 is a schematic diagram for explanation of another example of a state of transmitting and receiving an ultrasonic beams by a conventional system.

In this system, plural kinds of drive signals are fed to the ultrasonic transducer array 100. Thereby, from plural sets of pulsers, the plural kinds of drive signals are simultaneously fed to the plural ultrasonic transducers 101 included in the ultrasonic transducer array 100. For example, as shown in FIG. 15, two sets of timing pulses of pulse set A and pulse set B are applied to one set of elements, and both ultrasonic beam A and ultrasonic beam B are generated. Note that, in the case where one pulse of the pulse set A and one pulse of the pulse set B are superposed to each other, that forms a common pulse. These ultrasonic beams A and B are transmitted toward the object simultaneously in plural directions (for example, two directions).

In the above-described ultrasonic diagnosing method and ultrasonic diagnosing apparatus, recently, it is required that the resolution is improved and real time performance is improved by performing imaging at a higher speed. On this account, R. E. Davidsen et al. "TWO-DIMENSIONAL RANDOM ARRAYS FOR REAL TIME VOLUMETRIC IMAGING", ULTRASONIC IMAGING 16, 1994, pp. 143-163 discloses that the number of ultrasonic beams transmitted within a predetermined period is increased.

However, in the above references, the problem of crosstalk in the multi-beam transmission and reception is not considered, and conditions or means required to suppress crosstalk is not disclosed. Further, ideas for grasping an amount of crosstalk quantitatively by using a number of transmission beams or a number of receiving focal points as a parameter are not described.

SUMMARY OF THE INVENTION

The present invention has been achieved by considering the above-described circumstances. A first object of the present invention is to obtain image information with a high frame rate or a high volume rate. A second object of the present invention is to improve resolution in ultrasonic images.

In order to solve the above described problems, according to one aspect of the present invention, an ultrasonic imaging method of obtaining image information on a measurement target within an object to be inspected by transmitting ultrasonic beams toward the measurement target and receiving ultrasonic echoes reflected by the measurement target, comprises the steps of: (a) respectively transmitting plural ultrasonic beams toward plural directions within a predetermined period so that adjacent two ultrasonic beams are separated by not less than 20° from each other; and (b) processing plural detection signals obtained by detecting ultrasonic echoes so that plural receiving focal points are formed for each of the transmitted plural ultrasonic beams.

Further, according to one aspect of the present invention, an ultrasonic imaging apparatus for obtaining image information on a measurement target within an object to be inspected by transmitting ultrasonic beams toward the measurement target and receiving ultrasonic echoes reflected by the measurement target, comprises: an ultrasonic transducer array including plural ultrasonic transducers for transmitting ultrasonic waves in accordance with drive signals and receiving ultrasonic waves to output detection signals; transmitting signal processing means for supplying plural drive signals to the plural ultrasonic transducers, respectively; control means for controlling the transmitting signal processing means to respectively transmit plural ultrasonic beams from the ultrasonic transducer array toward plural directions within a predetermined period so that adjacent two ultrasonic beams are separated by not less than 20° from each other; receiving signal processing means for processing the plural detection signals respectively outputted from the plural ultrasonic transducers; and plural phase matching means, provided in correspondence with a number of the ultrasonic beams to be transmitted from the ultrasonic transducer array, for performing phase matching on the basis of the detection signals processed by the receiving signal processing means so that plural receiving focal points are formed for each of the transmitted plural ultrasonic beams.

According to the present invention, the amount of crosstalk, which is a basic problem in the complex multi-beam transmission and reception, can be obtained quantitatively on the basis of a simulation. Thereby, the number of times of transmitting and receiving ultrasonic beams per unit time can be increased while suppressing the amount of crosstalk, and therefore, ultrasonic imaging with a high frame rate or a high volume rate can be performed. Alternatively, the resolution in ultrasonic images can be improved.

DESCRIPTION OF THE PREFERRED EMBODIMENTS

Figure 1:
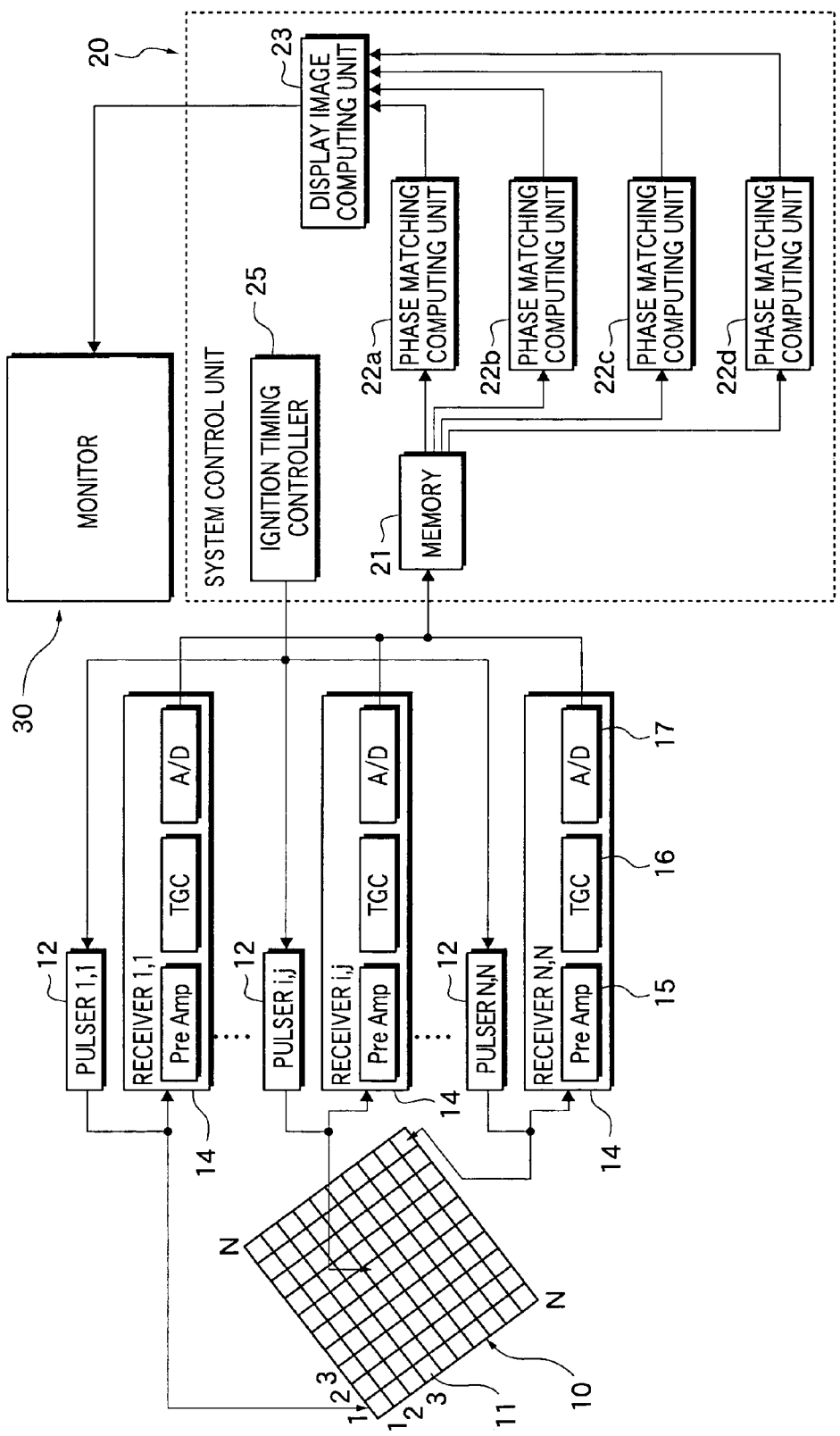
FIG. 1 is a block diagram showing a constitution of an ultrasonic imaging apparatus according to one embodiment of the present invention.

Now, referring to the drawings, an embodiment of the present invention will be described. Note that the same components are assigned with the same reference numerals and the description thereof will be omitted.

FIG. 1 is a block diagram showing a constitution of an ultrasonic transmitting and receiving apparatus. This ultrasonic imaging apparatus is used as an ultrasonic diagnosing apparatus or an industrial defect detecting apparatus, for example.

As shown in FIG. 1, this ultrasonic imaging apparatus has an ultrasonic transducer array 10 to be used in contact with an object to be inspected. The transducer array 10 shown in FIG. 1 is a so-called two-dimensional transducer array that includes plural (N×N=$N^2$) ultrasonic transducers 11 having a function of transmitting and receiving ultrasonic waves. In the ultrasonic transducer array 10, the plural ultrasonic transducers 11 are arranged in a two-dimensional matrix with N rows and M columns, for example. As the ultrasonic transducer 11, for example, a piezoelectric element made of PZT (lead zirconate titanate) or PVDF (polyvinylidene difluoride) is used. The piezoelectric element expands and contracts by being applied with a voltage, and generates an ultrasonic wave. On the other hand, the piezoelectric element expands and contracts by being applied with an ultrasonic wave, and generates an electric signal (detection signal).

Alternatively, such piezoelectric element is used as a transmitting element of ultrasonic waves, and a Fabry-Perot resonator (abbreviated as FPR), a fiber Bragg grating, or the like formed on each of the tips of the micro optical fibers is used as a receiving element of ultrasonic waves, and these may be combined to constitute the ultrasonic transducer array 10.

$N^2$ pulsers 12 and $N^2$ receivers 14 are connected to $N^2$ ultrasonic transducers 11, respectively.

Each pulser 12 is excited based on the output signal of an ignition timing controller 25 built in a system control unit 20, which will be described later, and outputs a drive signal to the corresponding ultrasonic transducer 11 of the ultrasonic transducer array 10. Each ultrasonic transducer 11 transmits an ultrasonic pulse to the object based on the drive signal inputted from the pulser 12, receives the ultrasonic pulse reflected from the object, and outputs a detection signal. These pulsers 12 are high speed pulsers capable of continuously outputting drive signals in a high cycle period (for example, 3 MHz to 10 MHz).

Each receiver 14 includes a preamplifier, a TGC (time gain compensation) amplifier 16, and an A/D converter 17. The detection signal outputted from each ultrasonic transducer 11 is subjected to analogue processing in the preamplifier 15 and the TGC amplifier 16 included in the corresponding receiver 14. By this analogue processing, the level of the detection signal is matched to the input signal level of the A/D converter 17. Each analogue signal outputted from the TGC amplifier is converted into a digital signal (data) by the A/D converter 17.

The system control unit 20 includes a memory 21, plural phase matching computing units 22a to 22d, a display image computing unit 23, and the ignition timing controller 25, and controls the entire system of the ultrasonic imaging apparatus.

Each pulser 12 is connected to the ignition timing controller 25. The ignition timing controller 25 outputs a signal for exciting each pulser 12. In the embodiment, the ignition timing controller 25 is constituted by an electronic circuit, however, it may be constituted by a pattern generator etc. The control of the ignition timing controller 25 enables transmission focusing processing for transmitting ultrasonic beams in plural directions from the ultrasonic transducer array 10.

The memory 21 is connected to the outputs of the plural receivers. The memory 21 temporarily stores the detection data outputted from the A/D converters 17 of the respective receivers.

The phase matching computing units 22a to 22d perform computation processing for matching phase of detection data stored in the memory 21. The phase matching computing units 22a to 22d are provided in correspondence with the number of the ultrasonic beams (transmitted beams) that are transmitted in parallel within a predetermined period (simultaneously or nearly simultaneously) from the ultrasonic transducer array 10. Here, the predetermined period specifically indicates a period several times longer than delay time used in the transmission focusing processing for forming transmitted beams by the ultrasonic waves transmitted from the plural ultrasonic transducers 11.

In this embodiment, since four ultrasonic beams are transmitted in parallel, four phase matching computing units 22a to 22d are provided. However, the number of phase matching computing units may be increased or decreased in correspondence with the number of the ultrasonic beams transmitted in parallel. Each system of the phase matching computing units 22a to 22d is constituted by a shift register delay line, a digital micro delay device, software, or a combination of these. Note that the phase matching computing units 22a to 22d are shown in single blocks with respect to each of the transmitted beams in FIG. 1, however, plural systems are provided according to the number of receiving focal points with respect to each transmitted beam.

The received beam forming by the phase matching computing unit 22a is performed as below. Each system of the phase matching computing unit 22a gives a predetermined delay to the detection data obtained based on the detection signal outputted from each ultrasonic transducer 11. Thereby, phases of the plural pieces of detection data, which have been obtained using a series of ultrasonic transducers 11 included in the ultrasonic transducer array 10, are matched. Further, the phase matching computing unit 22a digitally accumulates these pieces of detection data. Thus, by using the phase matching computing unit 22a having plural systems, reception focusing processing on plural transmitted beams can be simultaneously achieved.

The phase matching computing units 22b to 22d perform phase matching similarly to the phase matching computing unit 22a.

The display image computing unit 23 performs waveform detection of the detection signals, conversion into image data, predetermined image processing, and further, scanning format conversion on the data outputted from the phase matching computing units 22a to 22d. Thereby, image data in the sound beam data space is converted into the image data in the physical space. Furthermore, the display image computing unit 23 generates voxel data, which is data with respect to a certain volume, from sectional data for plural sheets, and performs computation for displaying a three-dimensional image.

The display image computing unit 23 is connected to a monitor 30. The monitor 30 converts image data having the scanning format converted in the display image computing unit 23 into an analogue signal by D/A conversion, and displays an image based on this signal.

Next, an ultrasonic imaging method according to the embodiment will be described.

Figure 2:
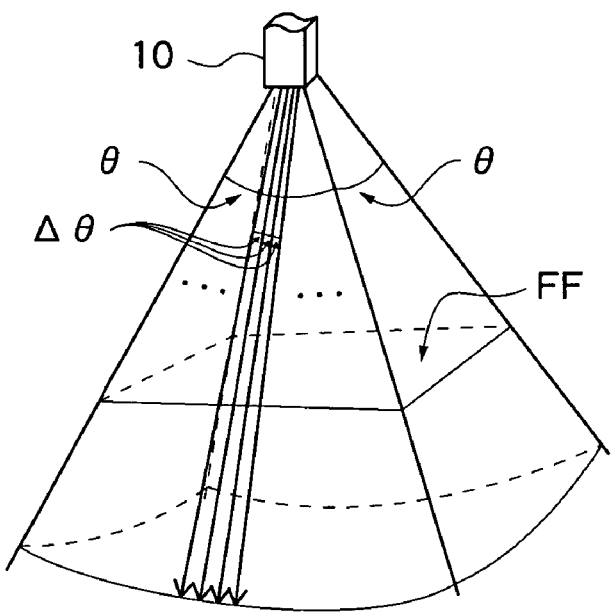
FIG. 2 is a diagram showing an imaging region within an object to be inspected.
Figure 3:
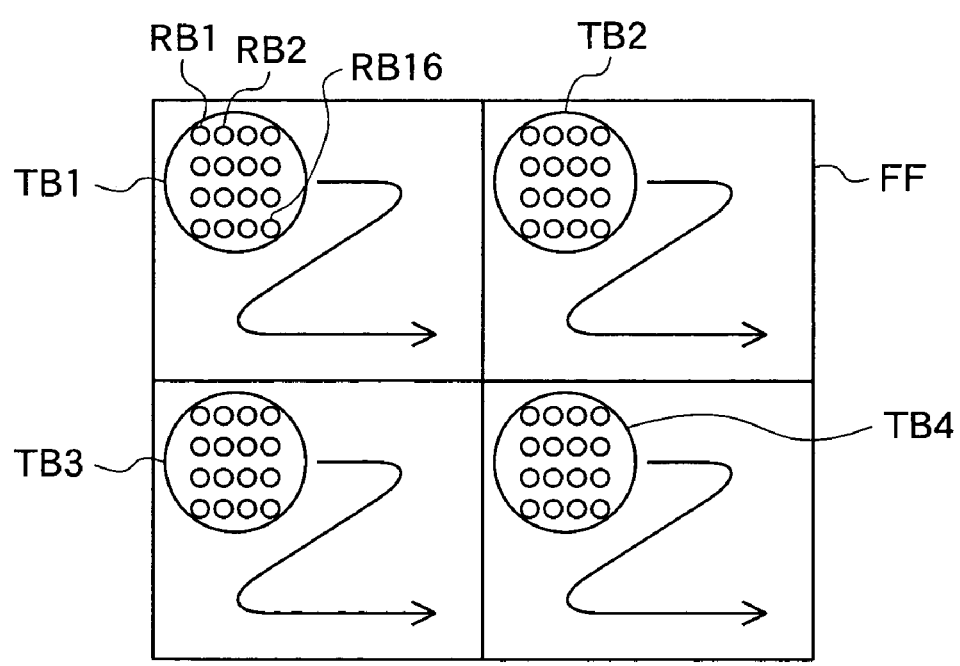
FIG. 3 is a diagram showing a focal plane of transmitted and received ultrasonic beams.

As shown in FIG. 2, an imaging region within the object is defined as a region expected by an angle θ with respect to one scanning direction, i.e., θ×θ with respect to orthogonal two scanning direction. In the embodiment, it is assumed that θ=45° to 90°. FIG. 3 shows a section (focal plane) FF at the focal points of the ultrasonic beams transmitted to the imaging region and the ultrasonic beams received from the imaging region.

In the embodiment, plural ultrasonic beams (transmitted beams) TB1 to TB4 are transmitted in parallel toward the imaging region within the object, and the reception focusing processing is performed when receiving ultrasonic echoes corresponding to the transmitted beams TB1 to TB4 respectively so that the ultrasonic echoes are divisionally received as plural received beams RB1 to RB16. Hereinafter, parallel transmission of plural ultrasonic beams is referred to as multi-beam transmission.

The reason for performing transmission and reception of ultrasonic beams as described above in the embodiment will be described as below.

For example, in the case where θ=60°, assuming that an angle interval Δθ of sampling in one scanning direction is 0.7°, which is necessary to obtain an elaborate ultrasonic image, the number of ultrasonic beams to be transmitted and received for scanning the entire imaging region is obtained by the following expression.

$$\text{(total number of beams)}=(\theta/\Delta\theta)\times(\theta/\Delta\theta)=(60/0.7)\times(60/0.7)\approx 7346 \quad (1)$$

In addition, in the case where the image data is acquired at the volume rate VOL=30 vol/sec in order to obtain an ultrasonic image in real time, the time period required for acquiring data per one volume becomes $1/30 \approx 33 \times 10^{-3}$ seconds. For example, in the case of imaging an organ etc. located at a depth $D_{OB}=15$ cm within the object, the round-trip distance an ultrasonic wave propagates within the object is 30 cm. Therefore, assuming the sound velocity $V_{US}=1540$ m/sec, the time period between transmitting and receiving an ultrasonic wave is given by the following expression.

$$0.3/1540=1.948\times10^{-4} \text{ sec} \quad (2)$$

Here, assuming that the ultrasonic beams are transmitted and received one by one to scan within the object, the number of times T at which the ultrasonic beams can be reciprocated within the time period for acquiring data per one volume is obtained by the following expression.

$$T=(33\times10^{-3})/(1.948\times10^{-4})\approx169 \quad (3)$$

In order to scan the entire imaging region, to perform transmission and reception of 7,346 ultrasonic beams at 169 times, the number of ultrasonic beams transmitted and received per one time is given by the following expression.

$$7346/169\approx43 \quad (4)$$

That is, 43 ultrasonic beams are transmitted and received toward the imaging region within the object in parallel at one time, by repeating this operation at 169 times, image data with respect to the entire image region can be collected within the time period for acquiring data per one volume.

Similarly, in the case where $\theta=90°$, the number of ultrasonic beams transmitted and received for scanning the entire imaging region becomes $(90/0.7)\times(90/0.7)\approx16530$. In this case, $16530/169\approx97$ of the ultrasonic beams are transmitted and received at one time, this operation may be repeated at 169 times.

Further, in the case where $\theta=45°$, the number of ultrasonic beams transmitted and received for scanning the entire imaging region becomes $(45/0.7)\times(45/0.7)\approx4133$. In this case, $4133/169\approx24$ of the ultrasonic beams are transmitted and received at one time, this operation may be repeated at 169 times.

However, for example, if 43 ultrasonic beams are transmitted in parallel toward the imaging region on the order of $60°\times60°$, intervals of the adjacent ultrasonic beams become narrow and cause to generate crosstalk. Therefore, in the embodiment, in order to obtain image data as to plural regions in parallel, the plural ultrasonic beams are subjected to multi-beam transmission, and reception focusing processing is performed on ultrasonic echoes corresponding to each transmitted beam to form plural receiving focal points so that ultrasonic echoes corresponding to one transmitted beam are divisionally received as plural received beams. For this purpose, the range of the number of ultrasonic beams transmittable in one multi-beam transmission and the range of the number of divisionally receivable ultrasonic beams have been considered.

First, the number of ultrasonic beams transmittable by one multi-beam transmission has been considered. In this case, if the intervals of adjacent ultrasonic beams are narrow, there arises the problem that the influence of side lobe becomes large and the reliability of image data becomes low. Therefore, the condition for suppressing the influence of side lobe to the degree not affecting image quality will be described. Note that "influence of side lobe" means that the ultrasonic echo, which is caused by a second transmitted beam adjacent to a first transmitted beam and reflected by a reflector in the transmitting direction, is added to the ultrasonic echo caused by the first transmitted beam.

Figure 4:
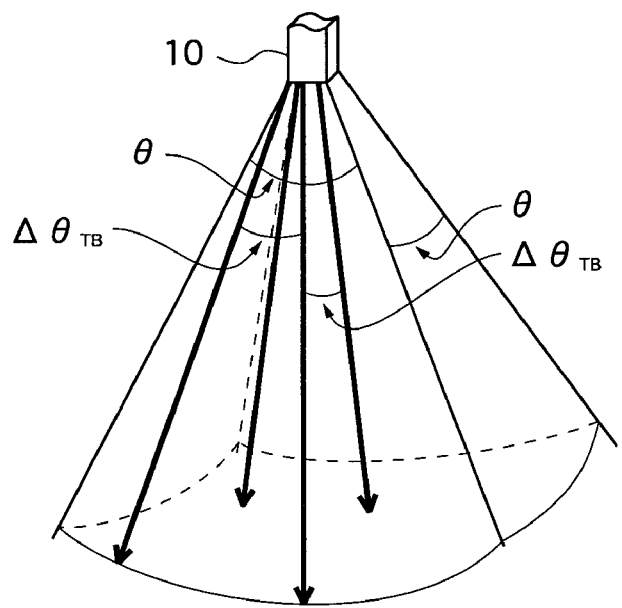
FIG. 4 is a diagram showing an interval $\Delta\theta_{TB}$ between adjacent plural transmitted beams in an imaging region expressed by θ×θ.
Figure 5:
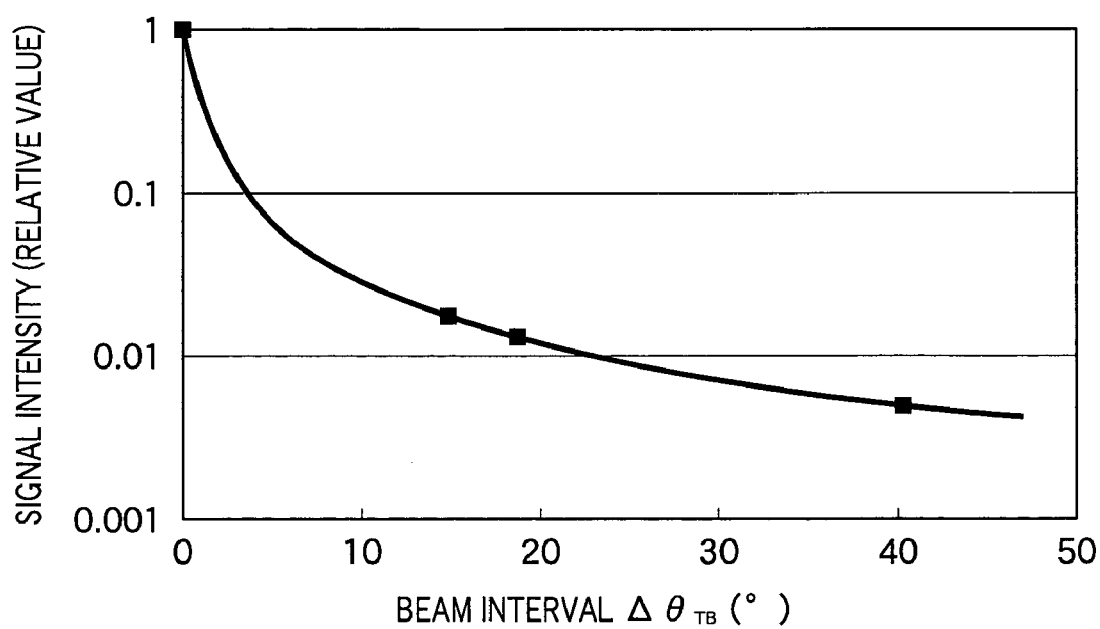
FIG. 5 is a graph showing the relationship between the interval between adjacent transmitted beams and intensity of a side lobe signal, which relationship is obtained by a simulation.

As shown in FIG. 4, in the case where plural ultrasonic beams are simultaneously transmitted to the imaging region represented by $\theta\times\theta$, the relationship between the interval of adjacent transmitted beams and the intensity of the side lobe signal is obtained by a simulation. In FIG. 5, the result of the simulation is shown. Note that "intensity of side lobe signal" means the intensity of the ultrasonic echo which is caused by a second transmitted beam adjacent to a first transmitted beam and reflected by a reflector in the transmitting direction and which is added to the ultrasonic echo caused by the first transmitted beam. In FIGS. 4 and 5, $\Delta\theta_{TB}$ shows the interval of adjacent transmitted beams and $I_{SL}(\Delta\theta_{TB})$ shows the intensity of the side lobe signal.

In addition, the curve as shown in FIG. 5 represents approximate expression obtained by performing regression analysis based on the simulation result. That is, the intensity of the side lobe signal $I_{SL}(\Delta\theta_{TB})$ is expressed by the following expression.

$$I_{SL}(\Delta\theta_{TB})=0.2/(\Delta\theta_{TB}+1)+0.8/(\Delta\theta_{TB}^2+1) \quad (5)$$

As shown in FIG. 5, it is seen that, when the interval of the adjacent transmitted beams becomes larger than 22°, the intensity of the side lobe signal becomes equal to or less than 0.01, and further, when the interval of the transmitted beam becomes equal to or more than 30°, the intensity of the side lobe signal becomes minimal. When the intensity of the side lobe signal $I_{SL}(\Delta\theta_{TB})\leq0.01$, the influence of side lobe on the ultrasonic image can be neglected.

Based on such simulation result, the condition is set that the interval of the adjacent transmitted beams is made equal to or more than 20°. Further, assuming that the imaging region is divided into Nt regions with respect to one direction, and the ultrasonic beams are transmitted one by one to each divided region, $\Delta\theta_{TB}$ is expressed as $\Delta\theta_{TB}=\theta/Nt$. Thereby, the following conditional expression is obtained.

$$\theta/Nt\geq20° \quad (6)$$

Transforming the expression (6), the following expression is obtained.

$$Nt\leq\theta/20°=0.05\cdot\theta \quad (7)$$

Substituting $\theta=45°, 60°, 85°$, and $90°$ into the expression (7), respectively, the upper limit of the number of transmitted beams in one direction of the imaging region is obtained as follows.

for $\theta=45°$, $Nt\leq2.25$ \quad (8a)

for $\theta=60°$, $Nt\leq3.00$ \quad (8b)

for $\theta=85°$, $Nt\leq4.25$ \quad (8c)

for $\theta=90°$, $Nt\leq4.50$ \quad (8d)

Figure 6:
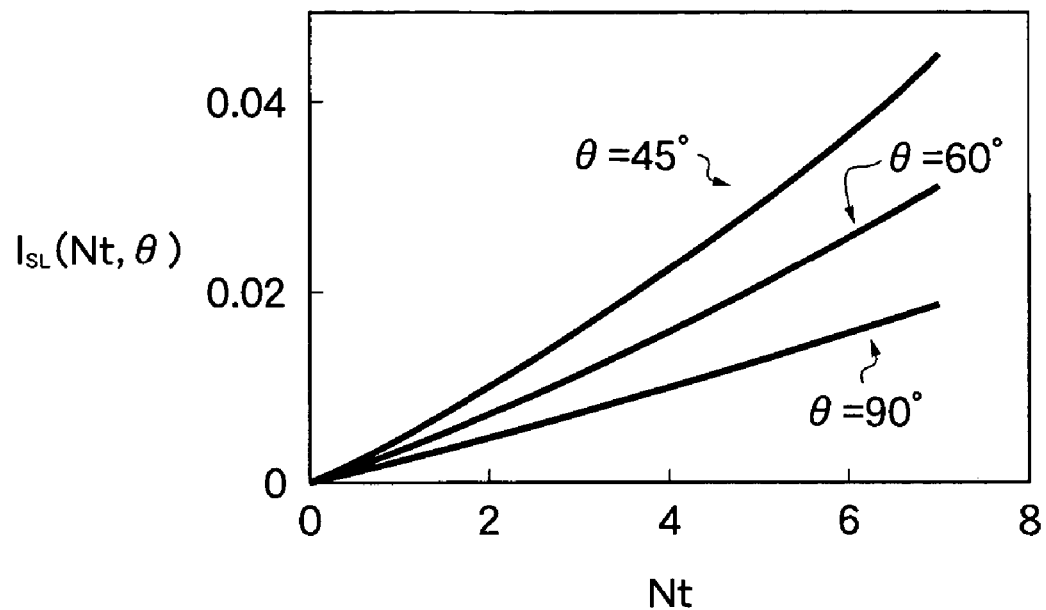
FIG. 6 is a graph showing the relationships between the number of transmitted beams and intensity of the side lobe signal in the case of θ=45°, 60°, and 90°.

FIG. 6 shows the relationship between the number of transmitted beams Nt and the intensity $I_{SL}(Nt,\theta)$ of the side lobe signal in the case where $\theta=45°, 60°$, and $90°$, which is obtained based on the expression (6). From the expressions (8a) to (8d) and FIG. 6, it is seen that the number of transmitted beams is desirably made as, Nt=1 to 2 for $\theta=45°$, Nt=2 to 3 for $\theta=60°$, and Nt=3 to 4 for $\theta=90°$. For example, in the case where $\theta=60°$ and Nt=2, the intensity of the side lobe signal becomes $I_{SL}(Nt,\theta)=I_{SL}(2,60)=7.3\times10^{-3}$, the influence of the side lobe can be practically neglected.

Therefore, with respect to the entire imaging region represented by $\theta\times\theta$, the number of transmitted beams may be equal to or less than $Nt^2$. For example, in the case where $\theta=60°$, the entire imaging region may be divided into $Nt^2=4$ regions, and multi-beam transmission may be performed toward the respective divided regions one by one, by the total $Nt^2$ of ultrasonic beams, and the imaging region may be scanned while maintaining intervals of adjacent transmitted beams.

In addition, it is conceivable that the diameter of the transmitted beam is made smaller in order to increase the number of the ultrasonic beams subjected to multi-beam transmission. However, in order to form the ultrasonic beam having smaller diameter, the aperture of the ultrasonic transducer array that generates ultrasonic waves should be made larger. On this account, since there is no choice but to enlarge the outside dimensions of the ultrasonic transducer array, it is undesirable that the operationality of the ultrasonic transducer array becomes lower and the construction becomes complex. Especially, that is unsuitable for an ultrasonic transducer array to be used in a manner in which it is pressed against an intercostal space when imaging a heart etc.

Next, a method of dividing the received ultrasonic echoes into plural received beams by computing processing such as phase matching has been considered. In this case, the number of divisionally receivable ultrasonic beams should be determined by considering temporal transmission intervals and time required for computing processing. That is, it is a precondition that the computing processing on the first received ultrasonic echoes should be completed by the time when the ultrasonic echoes corresponding to the next transmitted ultrasonic beam are received.

The processing time of the ultrasonic echoes can be calculated roughly as the following expression.

(processing time)=(number of clocks)×(number of steps)×(number of pieces of data) (9)

Where, the number of steps is generally three steps of reading out, adding, and writing. The number of pieces of data is represented by (number of elements)×(number of detection timings). The number of detection timings means the number of times the detection signals of the ultrasonic echoes are captured per unit time, i.e., axial resolution. For example, when the number of detection timings is doubled, the time interval for capturing the detection signals becomes half. That is, the distance interval for acquiring the image data with respect to the depth direction of the object is made half, which means that the axial resolution is improved twice higher.

From the expression (9), in the case where the received signals in the respective elements are subjected to serial processing with a clock signal of 100 MHz, the processing time is given as follows.

$(1×10^{-8})×3×(3000×512)=0.046$ sec

On the other hand, in the case where the received signals in the respective elements are subjected to parallel processing with a clock signal of 100 MHz, the processing time is given as follows.

$(1×10^{-8})×3×512=15.4×10^{-6}$ sec (10)

From the expressions (2) and (10), the number of times the computing processing can be repeated during a round trip of the ultrasonic beam in a region of the object having a depth of 15 cm is given as follows.

$(1.948×10^{-4})/(15.4×10^{-6})≈13$ times (11)

That is, the computation for forming the receiving focal point of the received ultrasonic echoes can be performed at 13 times.

In this case, by further promoting parallelism of the processing system of detection signals, it is possible to increase the number of computing processing during a round trip of the ultrasonic beam within the object, i.e., the number of received beams that can be divisionally received. However, since increase in lines subjected to parallel computing processing at high speed leads to cost increase of the apparatus, considering the balance between the real time performance and the cost, it is desirable that the number of divisionally receivable ultrasonic beams is set on about 16 at maximum.

Besides, the number of divisionally receivable ultrasonic beams is limited by the relation to the diameter of the transmitted beam.

Figure 7:
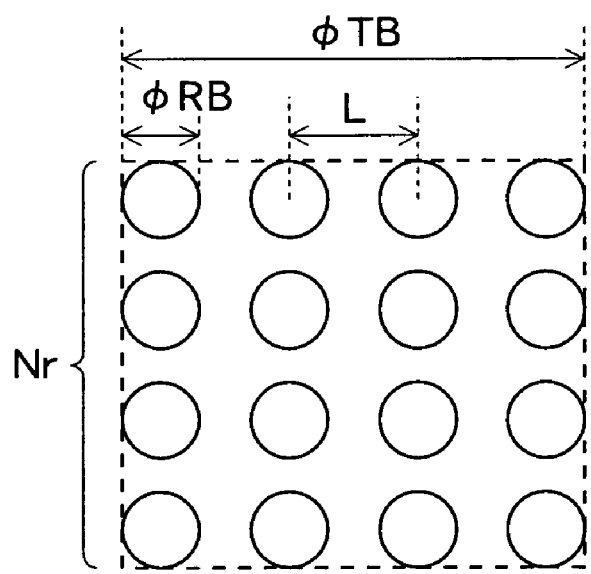
FIG. 7 is a diagram showing an arrangement of plural receiving focal points in the form of a tetragonal lattice in the case of divisional reception of an ultrasonic echo.
Figure 8:
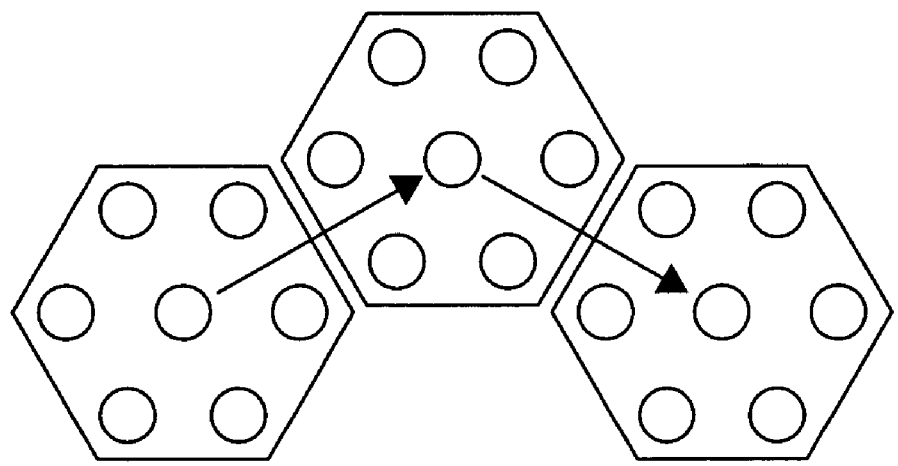
FIG. 8 is a diagram showing an arrangement of plural receiving focal points in the form of other than tetragonal lattices in the case of divisional reception of an ultrasonic echo.
Figure 9:
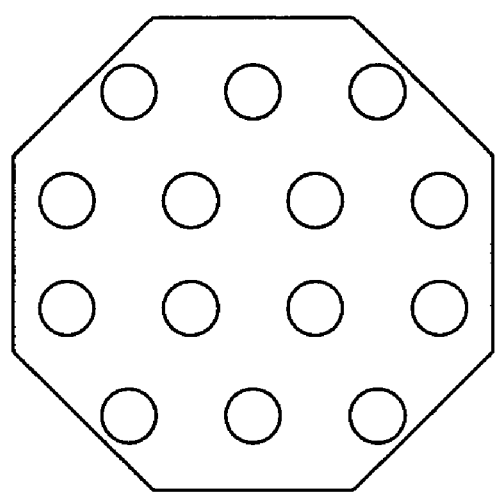
FIG. 9 is a diagram showing another arrangement of plural receiving focal points in the form of other than tetragonal lattices in the case of divisional reception of an ultrasonic echo.

Here, referring to FIG. 7, which shows an arrangement of plural receiving focal points on the focus plane FF in the case where the ultrasonic echoes corresponding to one transmitted beam TB are divisionally received as plural received beams RB. For one transmitted beam, the number of received beams in one scanning direction is expressed by Nr, and the number of all of the received beams is expressed by $Nr^2$. In the case of FIG. 7, Nr=4 and $Nr^2=16$. In FIG. 7, the receiving focal points are arranged in the form of tetragonal lattice, however, as shown in FIGS. 8 and 9, the focal points may be arranged not in the form of tetragonal lattice. In the case of FIG. 8, $Nr^2=7$, and in the case of FIG. 9, $Nr^2=14$.

As shown in FIG. 7, the diameter φTB of the ultrasonic beam TB to be transmitted is obtained as follows based on the diameter φRB and the interval of the received beams.

transmitted beam diameter φTB≈received beam diameter φRB+received beam interval L×(number of received beams in one direction Nr−1) (12)

Here, in the embodiment, in order to reduce crosstalk between the received beams, the received beam diameter φRB is set to the value in (half value of the peak of sound pressure)−6 dB. In addition, the received beam interval L represents a distance between centers of adjacent two received beams. For example, in the case where the received beams having a diameter of 3.5° are assumed to be arranged in 4×4 formation at a beam interval of 0.94° and divisionally received, the transmitted beam diameter is given as follows.

φTB=3.5+0.94×(4−1)≈6.3°

In order to increase the number of received beams to be divisionally received, it is conceivable that the transmitted beam diameter is enlarged while maintaining the received beam diameter constant. However, if the transmitted beam diameter is enlarged, the intensity largely varies in one transmitted beam and it becomes difficult to be used in ultrasonic imaging that requires high sound pressure in principle such as harmonic measurement and Doppler measurement, or ultrasonic imaging in which in-depth image data is obtained to details. Further, if the transmitted beam diameter is enlarged, the problem that the level of the received beam becomes lower in general imaging will occur. This is for the following reason.

The diameter φS of the ultrasonic transducer array and the transmitted beam diameter φTB are in inversely proportional relation to each other. Here, A is a constant defined by a wavelength of an ultrasonic wave.

φTB∝A/φS (13)

Thereby, considering the case where Nr=4 as a standard, the following relationship is derived. Here, φS(Nr) represents a diameter of the ultrasonic transducer array to be used when the transmitted beam having a diameter of φTB(Nr) is transmitted, and φS(4) represents a diameter of the ultrasonic transducer array to be used when the transmitted beam having a diameter of φTB(4) is transmitted.

φTB(Nr)/φTB(4)=φS(4)/φS(Nr)

Accordingly, the energy $I_{TB}$(Nr) of the transmitted beam is obtained as follows. Where, $I_0$ is a constant.

$$I_{TB}(Nr) = I_0 × φS(Nr)/φS(4)$$
$$= I_0 × φTB(4)/φTB(Nr)$$

Thereby, the energy density $σ_{TB}$(Nr) of the transmitted beam is expressed as follows.

$σ_{TB}(Nr)=I_{TB}(Nr)/φTB(Nr)$ (14)

Figure 10:
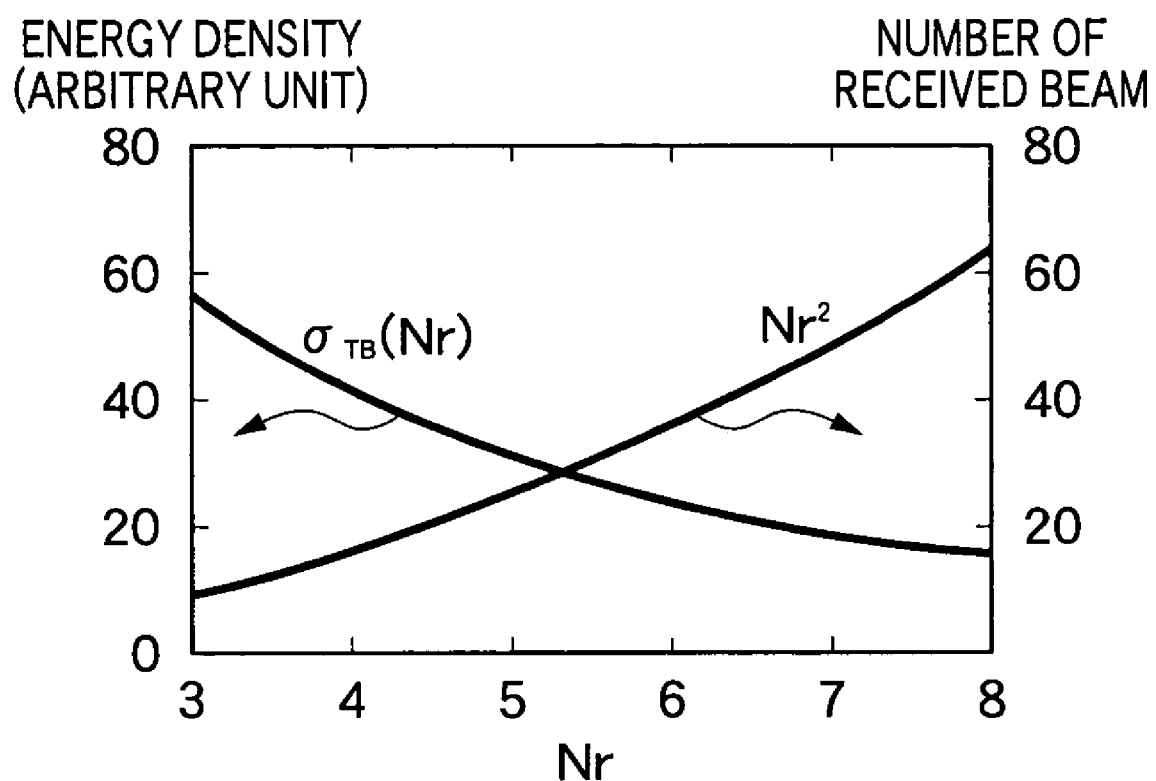
FIG. 10 is a graph showing the relationship between the number of received beams and energy density of transmitted beams.

FIG. 10 shows the relationship between the number of the received beams and the energy density of the transmitted beam, which is obtained based on the expression (14). As shown in FIG. 10, the more the number of the received beams is increased, the lower the energy density of the transmitted beam becomes. That is, in order to enlarge the transmitted beam diameter in accordance with the number of the received beams, it is necessary to make the aperture of the ultrasonic transducer array for forming ultrasonic beams smaller, thereby, the number of used ultrasonic transducers is reduced. Since the output of the entire transmitted beam is reduced and the energy density of the transmitted beam becomes lower, the levels of the respective received beams that are divisionally received are also reduced. Thus, in the case where the ultrasonic echoes corresponding to one transmitted beam are divisionally received, it is desired that the number of the received beams is set equal to or less than 16, i.e., Nr=2 to 4.

On the other hand, in order to increase the number of ultrasonic beams to be divisionally received, it is conceivable that the received beam diameter is made smaller while the transmitted beam diameter is maintained constant. However, in order to reduce the diameter of the receiving focal point, the detection signals obtained from a broader aperture are required, and therefore, the outside dimensions of the ultrasonic transducer array should be enlarged. Then, that is found to be unsuitable because the operationality of the ultrasonic transducer array is lowered and the construction thereof becomes complex.

As a result of the above consideration, the imaging region is divided into plural regions, multi-beam transmission is performed toward the respective regions with the interval between the adjacent transmitted beams separated at least 20°, and the received ultrasonic echoes are divisionally received as at most 16 received beams by computing processing in this embodiment.

Next, the number $S_{LN}(\theta, Nr)$ of pieces of image data, which is acquired by one multi-beam transmission and divisional reception of the ultrasonic echoes, is obtained.

$$S_{LN}(\theta,Nr)=\{\mathrm{trunc}(Nt(\theta))\cdot Nr\}^2 \quad (15)$$

or, $$S_{LN}(\theta,Nr)=\{\mathrm{trunc}(Nt(\theta))^2\}\cdot Nr^2 \quad (16)$$

Here, trunc(x) represents dropping the fractional portion of the number x to change the number x into an integer number, and $Nt(\theta)$ is a value obtained by the expression (7).

Figure 11:
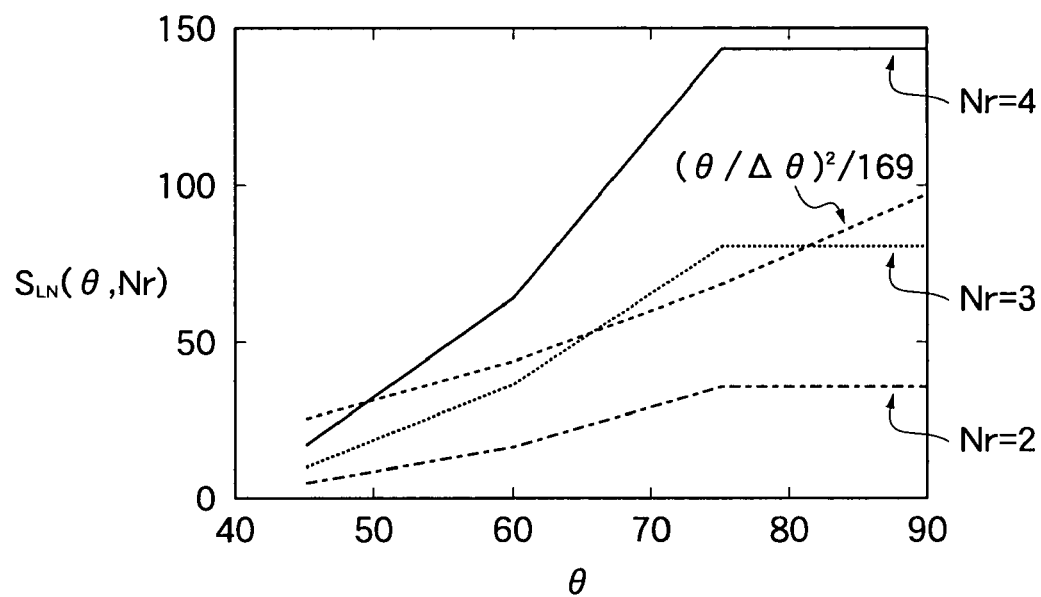
FIG. 11 is a graph showing the relationship between the imaging region and the number of pieces of image data obtained by one ultrasonic beam transmission and reception in the case where the receiving focal points are arranged in a tetragonal-lattice-form.
Figure 12:
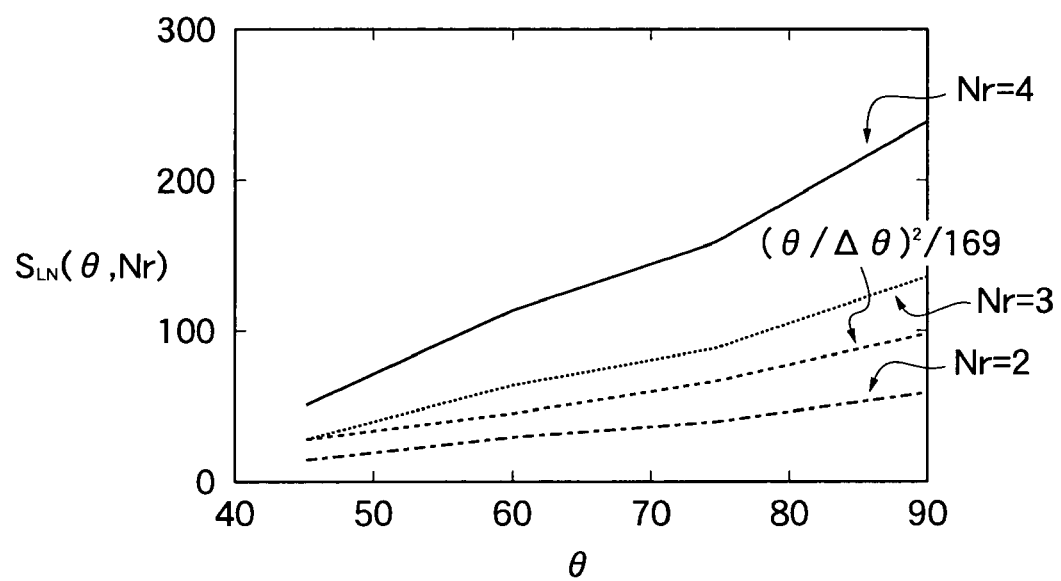
FIG. 12 is a graph showing the relationship between the imaging region and the number of pieces of image data obtained by one ultrasonic beam transmission and reception in the case where the receiving focal points are arranged not in the form of tetragonal lattice.

FIGS. 11 and 12 show the relationship between the range $\theta$ of the imaging region and the number of pieces of image data acquired by the one multi-beam transmission and divisional reception of the ultrasonic echo. FIG. 11 is obtained based on the expression (15) and FIG. 12 is obtained based on the expression (16).

By the way, from the expressions (1) to (4), in order to acquire image data regarding the entire imaging region at 30 vol/sec, it is necessary to reciprocate $(\theta/\Delta\theta)^2/169$ ultrasonic beams within the time period for acquiring volume data once. Here, $\theta$ is an angle of the imaging region in one scanning direction, $\Delta\theta$ is an angular interval of sampling in one scanning direction, and $(\theta/\Delta\theta)^2$ represents the number of ultrasonic beams required for scanning the entire imaging region. Therefore, from the expression (15), the number of pieces of image data, which is acquired by one multi-beam transmission and divisional reception of ultrasonic echo, is necessary to satisfy the following condition.

$$S_{LN}(\theta,Nr)\geq(\theta/\Delta\theta)^2/169 \quad (17)$$

As clearly seen from FIGS. 11 and 12, for Nr=4, the expression (17) is satisfied in almost all cases. Therefore, in the case where $\theta=60°$, for example, as shown in FIG. 3, multi-beam transmission may be performed on the imaging region toward $Nt^2=4$ regions, and the ultrasonic echoes corresponding to each transmitted beam may be divisionally received as $Nr^2=16$ received beams. Thereby, the same amount of image data as in the case where the 4×16=64 ultrasonic beams are transmitted and received can be acquired by one transmission and reception of ultrasonic beams.

Next, operation of the ultrasonic imaging apparatus according to the invention will be described by referring to FIGS. 1, 3, 13A, and 13B.

First, plural ultrasonic beams are transmitted toward different directions from the ultrasonic transducer array 10 shown in FIG. 1 within a predetermined period. That is, based on the control of the ignition timing controller 25 in the system control unit 20 shown in FIG. 1, drive signals are continuously outputted in a period of a high frequency (for example, 3 MHz to 10 MHz) from the plural pulsers 12 to the plural ultrasonic transducers 11 included in the ultrasonic transducer array 10. At that time, ultrasonic pulses maybe transmitted from all of $N^2$ ultrasonic transducers 11, or from limited some of these $N^2$ ultrasonic transducers. Alternatively, the $N^2$ ultrasonic transducers are divided in four areas, the ultrasonic beams may be formed one by one from the respective areas in accordance with the ultrasonic pulses transmitted from the plural ultrasonic transducers included in the respective areas. In either case, four beams are transmitted toward a measurement target within the object to be inspected from the ultrasonic transducer array.

Figure 13A:
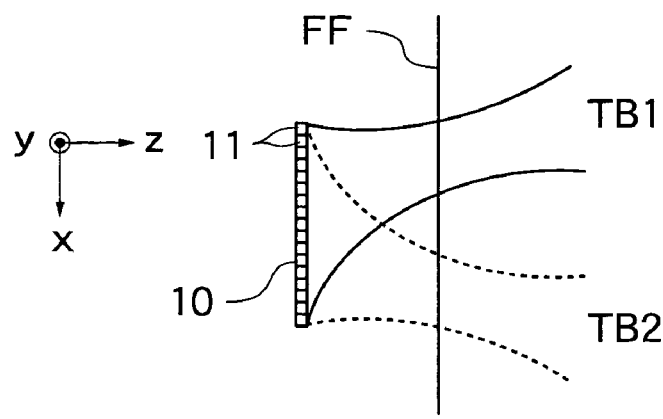
FIG. 13A is a diagram showing a state of performing multi-beam transmission on an ultrasonic beam from the ultrasonic transducer shown in FIG. 1.

As described above, the ultrasonic pulses transmitted from the ultrasonic transducer array form four transmitted beams TB1 to TB4 as shown in FIG. 3. Here, FIG. 13A shows two transmitted beams TB1 and TB2 of the four beams subjected to multi-beam transmission. The transmitted beams TB1 and TB2 become narrower as they travel in the region near the transmitting position, narrowest on the focus plane FF, and gradually broader afterwards. Accordingly, it is desirable that the operator appropriately operates the ultrasonic transducer array 10 so that the focal point F of the ultrasonic beam may fall on the measurement target within the object to be inspected.

The ultrasonic beams TB1 to TB4 transmitted from the ultrasonic transducer array 10 simultaneously or nearly simultaneously in four directions are reflected by the measurement target within the object, and the resulting ultrasonic echoes are received by the ultrasonic transducer array 10. The plural transducers 11 included in the ultrasonic transducer array 10 output detection signals based on the received ultrasonic echoes, respectively.

Next, reception focusing processing is performed on the detection signals outputted from the ultrasonic transducer array 10. That is, the respective detection signals outputted from the plural ultrasonic transducers 11 are inputted to the corresponding receivers 14, respectively. In the receiver 14, respective detection signals are subjected to analogue processing in the preamplifiers 15 and TGC amplifiers 16 to be matched to the input signal level of the A/D converters 17. Next, the analogue signals outputted from the TGC amplifiers 16 are converted into digital signals by the A/D converters 17, temporally stored in the memory 21, and then, inputted to the plural phase matching computing units 22 in parallel.

Figure 13B:
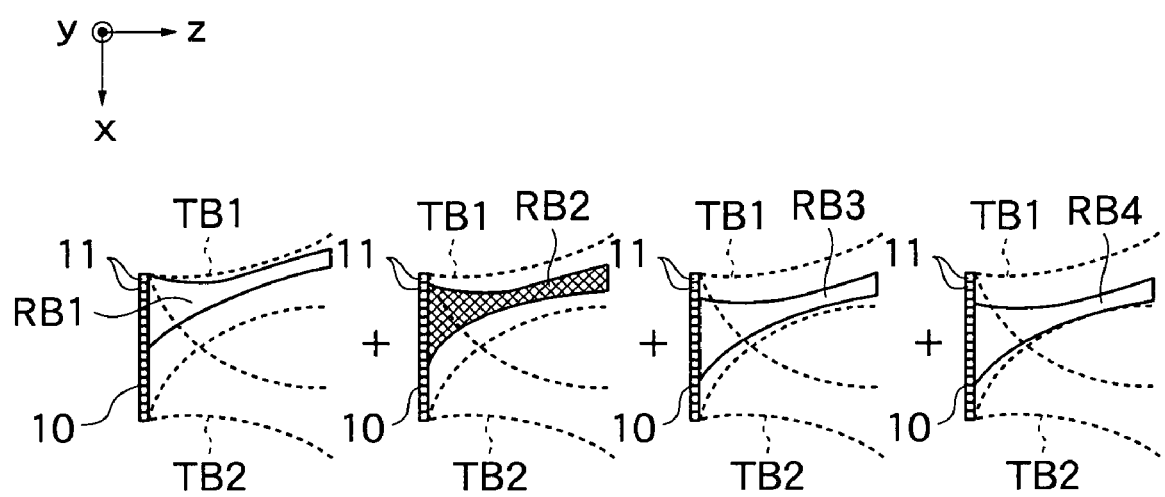
FIG. 13B is a diagram for explanation of a method of divisionally receiving the ultrasonic echoes as plural received beams.
Figure 14A:
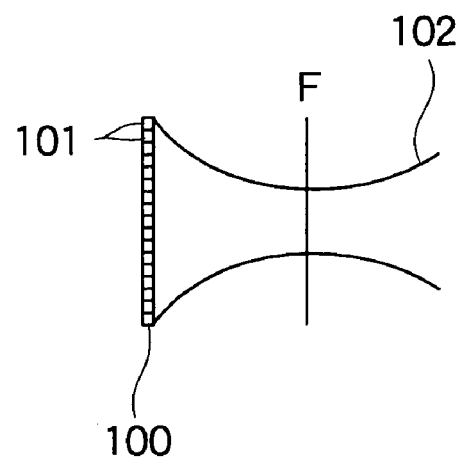
FIG. 14A is a schematic diagram for explanation of an example of a state of transmitting an ultrasonic beam by a conventional system.
Figure 14B:
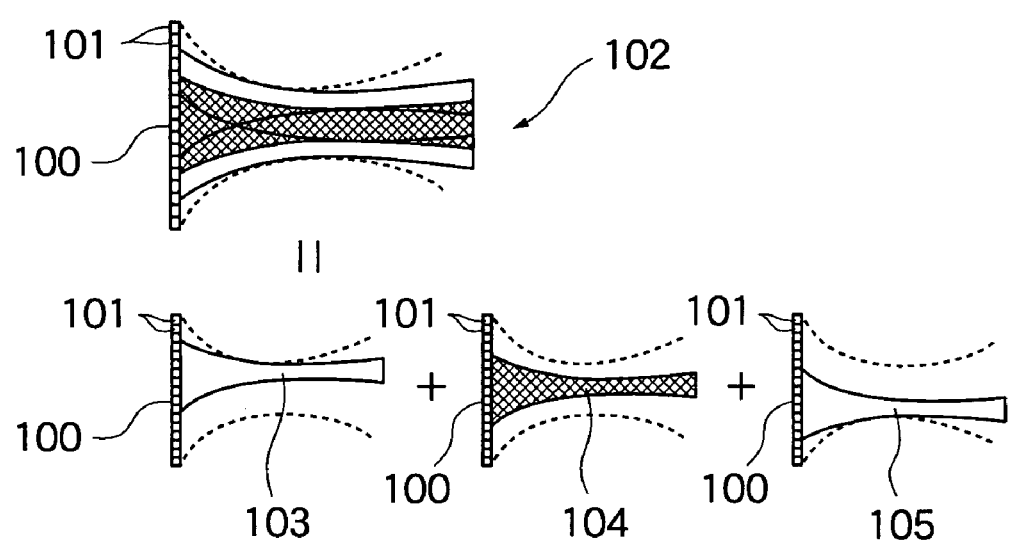
FIG. 14B is a schematic diagram for explanation of an example of a state of receiving an ultrasonic beam according to the conventional system.
Figure 15:
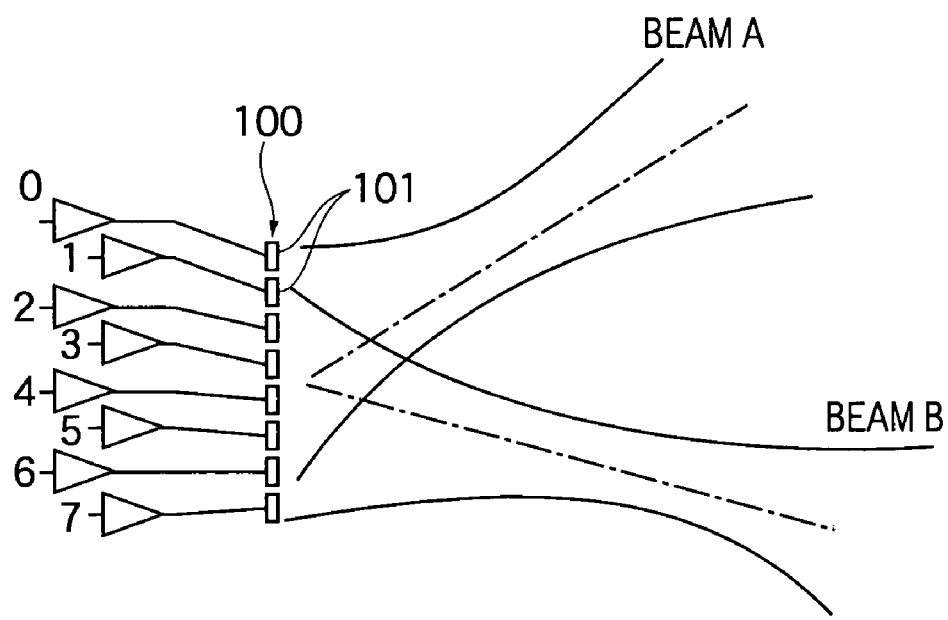
FIG. 15 is a schematic diagram for explanation of another example of a state of transmitting and receiving an ultrasonic beam according to a conventional system.
Figure 15:
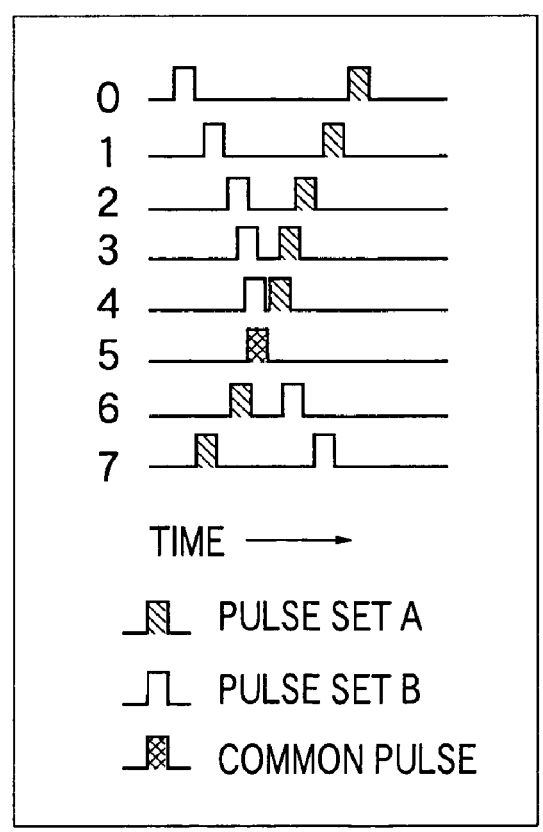

Next, the phase matching processing units 22a to 22d perform received beam forming based on the detection data obtained from the ultrasonic echoes. That is, using a series of detection data stored in the memory 21, the phase matching computing unit 22a provides the series of detection data with plural sets of delay corresponding to the number of receiving focal points, respectively, so that the received ultrasonic echoes corresponding to the transmitted beam TB1 may form 16 receiving focal points. Further, the phase matching computing unit 22a digitally accumulates the data provided with these plural sets of delay, respectively. Thereby, as shown in FIG. 13B, four received beams RB1 to RB4 are obtained with respect to one direction from the ultrasonic echoes corresponding to the transmitted ultrasonic beam TB1. Similarly, each of the phase matching processing units 22b to 22d performs received beam forming so that the received ultrasonic echoes corresponding to respective one of the transmitted beams TB2 to TB4 may form 16 receiving focal points. Thereby, as shown in FIG. 3, 16 received beams RB1 to RB16 are obtained from the ultrasonic echoes corresponding to each of the transmitted beams TB1 to TB4.

Further, by scanning within the respective regions using four transmitted beams while maintaining intervals between the adjacent transmitted beams, the multi-beam transmission of ultrasonic beams and the divisional reception of ultrasonic echoes are repeated.

As described above, the detection data subjected to received beam forming in the phase matching computing units 22a to 22d is subjected to waveform detection of the detection signals, conversion into image data, predetermined image processing in the display image computing unit 23, and further, the scanning format of the image data is converted. Thereby, the image data in the sound beam data space is converted into image data in the physical space. Furthermore, the display image computing unit 23 generates voxel data, which is data regarding a certain volume, from plural sheets of sectional data, and also performs computing for displaying a three-dimensional image. The result of computing of the display image computing unit 23 is converted into analogue signals and visually displayed in the monitor 30.

In the embodiment, the case where the ultrasonic imaging is performed on the imaging region represented by θ=60° is mainly described, however, ultrasonic imaging can be performed similarly on a narrower range or a broader range. For example, in the case where the imaging region is represented by θ=45° to 60°, the imaging region may be divided into two to four regions, and in the case where the imaging region is represented by θ=60° to 90°, the imaging region may be divided into four to nine regions. Thus, the ultrasonic beams are subjected to multi-beam transmission toward the respective regions, and the received ultrasonic echoes corresponding to each of the transmitted beams are divisionally received as 16 or less received beams by the receiving focus processing.

In addition, in the embodiment, a two-dimensional transducer array is used, however, other than that, one-dimensional or one and a half-dimensional transducer array or the like may be used. In that case, as well as the case described above, the ultrasonic beams are subjected to multi-beam transmission toward the plural regions divided in accordance with the imaging region, the ultrasonic echoes corresponding to each of the transmitted beam may be divisionally received as four or less received beams with respect to one scanning direction.

As described above, according to the embodiment, since the plural ultrasonic beams are simultaneously transmitted in multiple directions and the ultrasonic echoes corresponding to each transmitted beam are divisionally received as plural received beams, ultrasonic imaging with a high frame rate or a high volume rate can be performed. Alternatively, the resolution of ultrasonic images can be improved. At that time, by setting intervals of the plural ultrasonic beams transmitted in different directions to at least 20° or according to the size of the imaging region, crosstalk occurred between the plural ultrasonic beams can be suppressed, and thereby, high quality image data can be obtained. Further, according to the embodiment, the number of transmitted ultrasonic beams and the number of receiving focal points formed with respect to ultrasonic echoes are set in accordance with the scanning density for scanning the imaging region, the frame rate or the volume rate, the depth at which the measurement target exists within the object, the velocity of the ultrasonic beams or the like, so that high quality image data can be efficiently acquired in real time.

The invention claimed is:

1. An ultrasonic imaging method of obtaining image information on a measurement target within an object to be inspected by transmitting ultrasonic beams toward the measurement target and receiving ultrasonic echoes reflected by the measurement target, said method comprising the steps of:
    (a) respectively transmitting plural ultrasonic beams toward plural directions within a predetermined period so that adjacent two ultrasonic beams are separated by not less than 20° from each other; and
    (b) processing plural detection signals obtained by detecting ultrasonic echoes so that plural receiving focal points are formed for each of the transmitted plural ultrasonic beams.

2. An ultrasonic imaging method according to claim 1, wherein step (b) includes processing the plural detection signals so that not larger than 16 receiving focal points are formed for each of the transmitted plural ultrasonic beams.

3. An ultrasonic imaging method according to claim 1, wherein angles of an imaging region in orthogonal two scanning directions are 60°, and step (a) includes respectively transmitting four ultrasonic beams toward four directions within the predetermined period.

4. An ultrasonic imaging method of obtaining image information on a measurement target within an object to be inspected by transmitting ultrasonic beams toward the measurement target and receiving ultrasonic echoes reflected by the measurement target, said method comprising the steps of:
    (a) transmitting Nt ultrasonic beams with respect to a first scanning direction within a predetermined period toward an imaging region represented by an angle θ with respect to the first scanning direction; and
    (b) processing plural detection signals obtained by detecting ultrasonic echoes so that Nr receiving focal points are formed with respect to the first scanning direction for each of the transmitted ultrasonic beams;
    wherein Nt and Nr are set so as to satisfy a condition expression $(Nt \times Nr)^2 \geq (\theta/\Delta\theta)^2/T$, where Nt is an integer number that satisfies $Nt \leq 0.05 \cdot \theta$, $\Delta\theta$ represents an angle interval of sampling in the first scanning direction, and T represents a number of times ultrasonic beams are reciprocated within a time period for acquiring volume data once with respect to the imaging region.

5. An ultrasonic imaging method according to claim 4, wherein θ=60°, Nt =2, and Nr=4.

6. An ultrasonic imaging method of obtaining image information on a measurement target within an object to be inspected by transmitting ultrasonic beams toward the measurement target and receiving ultrasonic echoes reflected by the measurement target, said method comprising the steps of:

(a) transmitting $Nt^2$ ultrasonic beams within a predetermined period toward an imaging region represented by angles $\theta_1$ and $\theta_2$ with respect to two orthogonal directions, respectively; and (b) processing plural detection signals obtained by detecting ultrasonic echoes so that $Nr^2$ receiving focal points are formed for each of the transmitted ultrasonic beams;

wherein $Nt^2$ and $Nr^2$ are set so as to satisfy a condition expression $Nt^2 \times Nr^2 \geq (\theta_1/\Delta\theta) \cdot (\theta_2/\Delta\theta)/T$, where $Nt^2$ is an integer number that satisfies $Nt^2 \leq (0.05 \cdot \theta_1) \cdot (0.05 \cdot \theta_2)$, $\Delta\theta$ represents an angle interval of sampling in one scanning direction, and T represents a number of times ultrasonic beams are reciprocated within a time period for acquiring volume data once with respect to the imaging region.

7. An ultrasonic imaging method according to claim 6, wherein $\theta_1 = \theta_2 = 60°$, $Nt^2 = 4$, and $Nr^2 = 16$.

8. An ultrasonic imaging apparatus for obtaining image information on a measurement target within an object to be inspected by transmitting ultrasonic beams toward the measurement target and receiving ultrasonic echoes reflected by the measurement target, said apparatus comprising:

an ultrasonic transducer array including plural ultrasonic transducers for transmitting ultrasonic waves in accordance with drive signals and receiving ultrasonic waves to output detection signals;

transmitting signal processing means for supplying plural drive signals to said plural ultrasonic transducers, respectively;

control means for controlling said transmitting signal processing means to respectively transmit plural ultrasonic beams from said ultrasonic transducer array toward plural directions within a predetermined period so that adjacent two ultrasonic beams are separated by not less than 20° from each other;

receiving signal processing means for processing the plural detection signals respectively outputted from said plural ultrasonic transducers; and plural phase matching means, provided in correspondence with a number of the ultrasonic beams to be transmitted from said ultrasonic transducer array, for performing phase matching on the basis of the detection signals processed by said receiving signal processing means so that plural receiving focal points are formed for each of the transmitted plural ultrasonic beams.

9. An ultrasonic imaging apparatus according to claim 8, wherein said phase matching means performs the phase matching so that not larger than 16 receiving focal points are formed for each of the transmitted plural ultrasonic beams.

10. An ultrasonic imaging apparatus according to claim 8, wherein angles of an imaging region in orthogonal two scanning directions are 60°, and said control means controls said transmitting signal processing means to respectively transmit four ultrasonic beams from said ultrasonic transducer array toward four directions within the predetermined period.

11. An ultrasonic imaging apparatus for obtaining image information on a measurement target within an object to be inspected by transmitting ultrasonic beams toward the measurement target and receiving ultrasonic echoes reflected by the measurement target, said apparatus comprising:

an ultrasonic transducer array including plural ultrasonic transducers for transmitting ultrasonic waves in accordance with drive signals and receiving ultrasonic waves to output detection signals;

transmitting signal processing means for supplying plural drive signals to said plural ultrasonic transducers, respectively;

control means for controlling said transmitting signal processing means to transmit Nt ultrasonic beams with respect to a first scanning direction within a predetermined period from said ultrasonic transducer array toward an imaging region represented by an angle $\theta$ with respect to the first scanning direction;

receiving signal processing means for processing the plural detection signals respectively outputted from said plural ultrasonic transducers; and plural phase matching means for performing phase matching on the basis of the detection signals processed by said receiving signal processing means so that Nr receiving focal points are formed for each of the transmitted plural ultrasonic beams with respect to the first direction;

wherein said control means sets Nt and Nr so as to satisfy a condition expression $(Nt \times Nr)^2 \geq (\theta/\Delta\theta)^2/T$, where Nt is an integer number that satisfies $Nt \leq 0.05 \cdot \theta$, $\Delta\theta$ represents an angle interval of sampling in the first scanning direction, and T represents a number of times ultrasonic beams are reciprocated within a time period for acquiring volume data once with respect to the imaging region.

12. An ultrasonic imaging apparatus for obtaining image information on a measurement target within an object to be inspected by transmitting ultrasonic beams toward the measurement target and receiving ultrasonic echoes reflected by the measurement target, said apparatus comprising:

an ultrasonic transducer array including plural ultrasonic transducers for transmitting ultrasonic waves in accordance with drive signals and receiving ultrasonic waves to output detection signals;

transmitting signal processing means for supplying plural drive signals to said plural ultrasonic transducers, respectively;

control means for controlling said transmitting signal processing means to transmit $Nt^2$ ultrasonic beams within a predetermined period from said ultrasonic transducer array toward an imaging region respectively represented by angles $\theta_1$ and $\theta^2$ with respect to two orthogonal scanning directions;

receiving signal processing means for processing the plural detection signals respectively outputted from said plural ultrasonic transducers; and plural phase matching means for performing phase matching on the basis of the detection signals processed by said receiving signal processing means so that $Nr^2$ receiving focal points are formed for each of the transmitted plural ultrasonic beams;

wherein said control means sets $Nt^2$ and $Nr^2$ so as to satisfy a condition expression $Nt^2 \times Nr^2 \geq (\theta_1/\Delta\theta) \cdot (\theta_2/\Delta\theta)/T$, where $Nt^2$ is an integer number that satisfies $Nt^2 \leq (0.05 \cdot \theta_1) \cdot (0.05 \cdot \theta_2)$, $\Delta\theta$ represents an angle interval of sampling in one scanning direction, and T represents a number of times ultrasonic beams are reciprocated within a time period for acquiring volume data once with respect to the imaging region.

13. An ultrasonic imaging apparatus according to claim 11, wherein $\theta = 60°$, $Nt = 2$, and $Nr = 4$.

14. An ultrasonic imaging method according to claim 12, wherein $\theta_1 = \theta_2 = 60°$, $Nt^2 = 4$, and $Nr^2 = 16$.

* * * * *